United States Patent [19]

Houlihan et al.

[11] 4,083,871
[45] Apr. 11, 1978

[54] PREPARATION OF 2-SEC.-ALKYLAMINOBENZOPHENONES

[75] Inventors: William J. Houlihan, Mountain Lakes, N.J.; Paul G. Mattner, Brooklyn, N.Y.; Joseph A. Smith, Fanwood, N.J.

[73] Assignee: Sandoz, Inc., E. Hanover, N.J.

[21] Appl. No.: 653,361

[22] Filed: Jan. 29, 1976

[51] Int. Cl.$^2$ .............................................. C07C 85/08
[52] U.S. Cl. .......................... 260/570 AB; 260/340.3; 260/340.5 R; 260/566 F
[58] Field of Search ............ 260/570 AB, 340.5, 340.3

[56] References Cited
PUBLICATIONS

Gribble et al., "Journal American Chemical Society", vol. 96, pp. 7812–7814 (1974).
Borch et al., "Journal American Chemical Society", vol. 91, pp. 3996–3997 (1969).

*Primary Examiner*—Robert V. Hines
*Attorney, Agent, or Firm*—Gerald D. Sharkin; Richard E. Vila

[57] ABSTRACT

2-Sec.-alkylaminobenzophenones are prepared by reacting a corresponding 2-aminobenzophenone with a ketone, a borohydride and carboxylic acid.

26 Claims, No Drawings

PREPARATION OF 2-SEC.-ALKYLAMINOBENZOPHENONES

Compounds such as 2-alkylaminobenzophenones are chemical intermediates of great and increasing importance, such as in the preparation of pharmacologically active compounds. The efficient preparation of such phenyl ketones is therefore of corresponding high importance and has been more difficult or costly than might be expected considering the interest in such compounds and their relatively simple structure. A problem area has been the sec.-alkylamino groups in terms of how and when the same can be best created or introduced in the overall synthesis. A recent development limited to isopropylamino compounds which are of substantial interest in preparation of the anti-inflammatory quinazolinones of type disclosed in U.S. Pat. No. 3,723,432 is described in U.S. Pat. No. 3,845,128 and is believed to provide a substantial improvement over prior procedures. However, this process nevertheless still relies upon the use of alkyl halides which are relatively expensive and also tends to involve rather lengthy reactive times.

The principal object of the present invention is to provide a new and more efficient process for the preparation of 2-sec.-alkylaminobenzophenones.

Briefly stated, the present invention involves the preparation of 2-sec.-alkylaminobenzophenones by reacting a corresponding 2-aminobenzophenone, a ketone, a borohydride and carboxylic acid having a pH of from 3.0 to 5.0. The reaction provides particularly high yields and is surprisingly efficient, especially in view of the known ability of the borohydrides to reduce benzophenones to their corresponding benzhydrols.

More particularly, the process of the present invention involves the preparation of 2-sec.-alkylaminobenzophenones of the formula I:

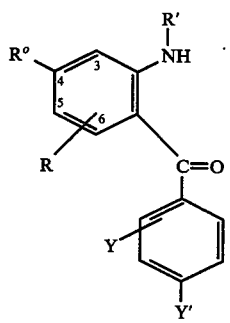

wherein
R' is a secondary alkyl of 3 to 5 carbon atoms,
R and R⁰ are independently hydrogen, halo of atomic weight of from 18 to 36, i.e., fluoro or chloro, straight chain alkyl of 1 to 4 carbon atoms, straight chain alkoxy of 1 to 4 carbon atoms or trifluoromethyl, with the provisos that R is in the 5- or 6-position, and no more than one of R and R⁰ is trifluoromethyl, or
R⁰ and R together form 4,5-alkylenedioxy of 1 to 2 carbon atoms, and
Y and Y' are independently hydrogen, halo of atomic weight of from 18 to 36, i.e., fluoro or chloro, straight chain alkyl of 1 to 4 carbon atoms, straight chain alkoxy of 1 to 4 carbon atoms or trifluoromethyl, with the proviso that no more than one of Y and Y' is trifluoromethyl, by reacting together a borohydride, carboxylic acid, a corresponding 2-aminobenzophenone of the formula II:

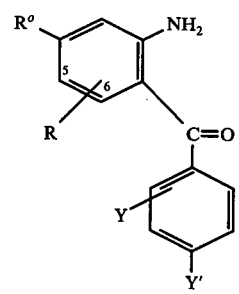

wherein R⁰, R, Y and Y' are as above defined, and a compound of the formula III

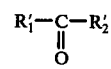

wherein $R_1'$ and $R_2'$ are each alkyl of 1 to 3 carbon atoms with the proviso that $R_1'$ and $R_2'$ do not exceed 4 carbon atoms.

The carboxylic acids employed in the invention may, for purposes of definition, be defined as those saturated acids having from 2 to 4 carbon atoms and a strength of from pH 3.0 to 5.0 in a 98% by weight aqueous solution, preferably a pH between 3.5 to 5.0 in such solution, and more preferably a pH of from 4.0 to 4.6. The preferred acids are the well known monocarboxylic acids, such as acetic acid and propionic acid. The particularly preferred acid is acetic acid. It is to be understood that the term "carboxylic acid" as used herein is intended to indicate only those acids which contain only carbon and hydrogen in addition to at least one carboxy group.

The borohydrides employed in the invention are those well known as reducing agents, i.e., the reducing borohydrides. The particularly suitable borohydrides are the alkali metal borohydrides, in which the alkali metal is the only metal, particularly the borotetrahydrides such as lithium borohydride, sodium borohydride, and potassium borohydride, more preferably sodium or potassium borohydride, particularly sodium borohydride.

Certain of the reaction conditions and parameters and/or their relationship to each other, are deemed critical or important in successfully carrying out the process of the present invention, as will be hereinafter disclosed and discussed.

The process of the present invention may be carried out at temperatures in the range of from 10° C. to plus 35° C., preferably 15° C. to 30° C., and more preferably at temperatures of from 15° C. to 28° C. Below about 10° C. undesirably slow reaction rates are encountered. The upper temperature limit of 35° C. is critical in order to avoid substantial hydrol formation which is detected at about 30° C. and which rapidly increases above 35° C.

The amount of borohydride employed in the reaction may be expressed relative to the amount of the compound II. In general, satisfactory results are obtainable when the mol ratio of borohydride to the compound II is at least 1.7:1. On the other hand, mol ratios in excess of 4:1 result in increased undesired benzhydrol formation. Preferably, the mol ratio is in the range of from 2:1 to 3.2:1, and desirably in the range of from 2:1 to 2.8:1. It has also been found important for best results to employ the borohydride in finely divided form thereby avoiding the use of pellets and the like. Suitable such forms have a particle size which passes through a Tyler Standard Screen No. 20, preferably through a No. 60 Tyler Standard Screen. Desirably, the borohydride is employed in powdered form.

It is essential to employ an excess of acid relative to the borohydride on a mol equivalent basis in order to avoid formation of substantial amounts of undesired hydrolby-product. For this reason and since the acid also serves as a co-solvent for the reaction, the actual amount of carboxylic acid employed will be fairly substantial. Hence, the amount of acid relative to the compound II is suitably represented by an actual or absolute mol ratio of at least about 6:1. The upper limit on the amount of carboxylic acid is not critical and its determined more by the requirements of space and other practicalities. In general, mol ratios of acid to the compound II in excess of 50:1 tend to become impractical and are avoided. Preferably, the mol ratio is in the range of from 8:1 to 30:1, more preferably 10:1 to 20:1.

The process is carried out in a solution of cosolvents comprising an excess of the compound III and the carboxylic acid. Only one mol of compound III is necessary in theory to conduct the alkylation of the invention. It has been found important to employ an amount of the compound III which may be expressed in terms of a mol ratio of the compound III to the compound II of at least 3:1. The mol ratio of total compound III to compound II is more suitably at least 4:1 and preferably at least 6:1, more preferably from 8:1 to 30:1 and desirably from 10:1 to 20:1. The upper limit on the amount of the compound III is not critical and is again more controlled by the limitations of space and other practicalities. Mol ratio in excess of 50:1 offer no prospect of additional advantages and are generally avoided. Other organic solvents which are inert in the sense of not having a deleterious effect on the reaction may be added, if desired, although no particular additional benefits are foreseen by reason of such addition. Such additional solvents include the alcohol analogs of the compound III employed. Examples of such solvents include the common ethers and the like, such as dioxane and tetrahydrofuran and isopropanol. The character and quantities of all solvent components including the excess carboxylic acid are such that the reaction is carried out in a substantially homogeneous solution, i.e., the compound II and any intermediate products leading to the desired product are dissolved in other liquid components of the reaction system and together therewith from such homogeneous solution. Hence, the actual amounts of the carboxylic acid, compound III and any other liquid present are such and proportioned to each other and to the compound II so that the reaction is carried out in a substantially homogeneous solution within the indicated temperature range. Failure to maintain the compound II and any intermediate products in solution will also result in undesired benzohydrol formation. Besides the inclusion of additional solvents, the reaction mixture may contain other agents which do not have a deleterious effect on the reaction, although the reaction system preferably consists of the compounds II and III, the carboxylic acid, water and the borohydride. The inclusion of substantial amounts of agents having a buffering effect is, however, avoided since the reaction system desirably has an acid pH between 3.0 to 5.0. The carboxylic acid employed will normally contain small amounts of water which can be tolerated in the reaction without adverse effect. However, it has been found that water in substantial quantities does adversely affect the reaction and is avoided. Hence, the reaction is carried out in the presence of no more than about 8% water by weight based on the weight of carboxylic acid employed in order to achieve yields of at least 70%. Desirably, the reaction is carried out in no more than 5% water by weight based on the weight of the acid. The reaction is conveniently effected in a solution containing from 0.1% to 2.5% of water by weight of the carboxylic acid.

In general, the reaction is carried out by establishing a solution prepared by mixing the compounds II and III and carboxylic acid, and then adding borohydride thereto. The rate of addition of the borohydride has been found to have an influence on the reaction in terms of avoiding substantial undesired benzhydrol formation. The influence of the rate of addition varies with the solution temperature at which the addition is made with the faster rates more tolerable at the lower reaction or solution temperatures. Hence, in general, the addition, which is exothermic and suitably involves several or continuous additions at a temperature of at least 10° C., is controlled at a rate such that the resulting reaction solution is maintained at a temperature not exceeding 35° C., and desirably does not increase by more than 10° C. by reason of such addition. Preferably, the addition takes place at a temperature of at least 15° C. and is controlled at a rate such that the resulting reaction solution is maintained at a temperature not exceeding 30° C., and more preferably such that the temperature does not increase more than 5° C. by the addition. It is particularly preferred that the addition take place at a temperature of at least 15° C. and is controlled at a rate such that the resulting reaction solution is maintained at a temperature not exceeding 28° C. and the actual temperature increase by reason of such addition is not more than 2° C. In each of the above cases, the temperature of the reaction solution is maintained within required or preferred temperature ranges throughout the reaction including any period subsequent to such addition. The time of addition will span a time period of at least 30 minutes, preferably at least 50 minutes. The number and size of portions added in portionwise addition (or rate in continuous addition) is suitably determined by the temperature rise caused by or desired during the addition, e.g., the more preferred temperature rise does not exceed 5° C. and it is particularly preferred to avoid a rise in excess of 2° C. Total reaction time commencing with borohydride addition and terminating with the removal of desired product from the reaction solution which contained or contains the borohydride is generally from 40 minutes to not more than 10 hours and desirably should not exceed 10 hours if unreacted borohydride remains in the reaction solution after such period. The reason for such desired control of reaction time is that the borohydride will slowly effect a reduction of the desired product to the corresponding and undesired benzhydrol. Accordingly, significant undesired benzhydrol formation is avoided by limiting reaction time to no more than 10 hours. More preferably the reaction is terminated within no more than than two hours after chromatography shows essentially no further desired alkylation of the compound II. More usually, reaction time are in the range of 1 to 4 hours. The 10 or less hour reaction time for the process of the invention represents a further advantage over the process described in U.S. Pat. No. 3,845,128.

The desired product of the formula I may be recovered from the reaction solution by working up by conventional procedures.

In general, the reaction may be readily carried out to provide good yields of the order of at least 70% on a molar basis, and high yields of the order of at least 85%, generally from 80% to about 100%, more usually 90% to 99%, are readily obtainable under the more preferred operating conditions.

The process of the invention is particularly preferred for isopropylations.

The process of the present invention may also be understood as proceeding through an intermediate which is formed on combining the compounds of the formulae II and III and the carboxylic acid; the intermediate being reduced on the introduction of the borohydride to form the desired product of the formula I, said intermediate being represented structurally by the formula IIa:

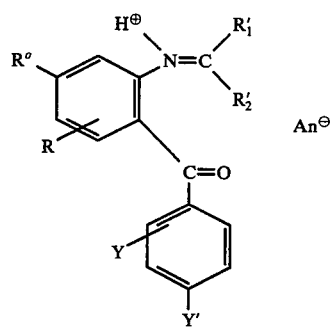

IIa wherein R, $R^0$, Y, Y', $R_1'$ and $R_2'$ are as above defined and An is the anionic form of the carboxylic acid. Accordingly, the compounds I may also be prepared in accordance with the invention by subjecting a compound of the formula IIa in a carboxylic acid containing homogeneous solvent solution to borohydride reduction by adding a borohydride to such homogeneous solution in the manner and under the temperature conditions hereinbefore disclosed, the mol ratios of borohydride to the compound IIa being the same as hereinabove disclosed for the mol ratios of borohydride to the compound II. The homogeneous solution of the compound IIa may, of course, be provided as also hereinbefore discussed by combining the compounds II and III, the carboxylic acid and any additional inert solvents desired to be employed. In any event, said homogeneous solution will contain a carboxylic acid (as hereinbefore defined) in a mol ratio of at least 6:1 as determined by the number of mols of carboxylic acid aniona (associated or dissociated) presence per mol of said compound IIa. Stated otherwise, the solution contains a carboxylic acid as defined herein in a mol ratio of at least 5:1 plus the one mole of such acid or its equivalent as represented by An, as above defined. Preferably, said solution will contain as a cosolvent a compound III in a mol ratio to the compound IIa of at least 2:1, more suitably at least 3:1, more preferably at least 6:1, desirably from 7:1 to 29:1 and more desirably from 9:1 to 19:1. Also, it is particularly preferred that such solution contain no more than 8% water by weight based on the weight of the carboxylic acid presence as determined as stated immediately above by the number of mols of carboxylic anions present in the solution. More preferably the solution contains no more than 5% water, but typically between 0.1% to 2.5% water by weight of the carboxylic acid.

The compounds of the formulae II and III are each well known or may be prepared from known materials by established procedures.

The following examples are given for purposes of illustration and discussion only, the borohydride in all cases being used in powdered form.

EXAMPLE 1

Preparation of 2-(N-isopropylamino)-4-methylbenzophenone

To a solution of 21.1 gms. of 2-amino-4-methylbenzophenone in 100 mls. of acetone is added 100 mls. of glacial acetic acid. The solution is cooled to 20° C. With stirring, and by portionwise addition, 10 gms. of sodium borohydride is added to the solution over a period of 70 minutes. After the addition, the solution is stirred for an additional 20 minutes at 20° C., and extracted with 100 mls. of chloroform and 50 mls. of water. The aqueous phase is extracted twice using 50 mls. of chloroform each time. All the chloroform solutions are then combined and treated with 150 mls. of 20% ammonium hydroxide. The chloroform phase is dried over magnesium sulphate, filtered and concentrated by distillation to a constant weight of 25 gms or a crude 99% yield of 2-(N-isopropylamino)-4-methylbenzophenone, providing an actual yield of pure material of at least 90%.

EXAMPLE 2

Example 1 is repeated except that a mol equivalent amount of propionic acid is substituted for the acetic acid to obtain a high yield of at least 85% of 2-(N-isopropylamino)-4-methylbenzophenone.

EXAMPLES 3-5

Example 1 is repeated except that the reaction system contains amounts of water equivalent to introducing the acetic acid in the form of aqueous solution having a concentration of 90% by weight, 60% by weight and 36% by weight to obtain respectively yields of 59%, 27% and 9% of 2-(N-isopropylamino)-4-methylbenzophenone.

What is claimed is:

1. The process for preparing in at least 75% yield a 2-sec.-alkylaminobenzophenone of the formula:

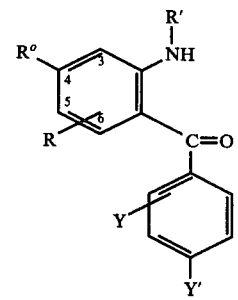

wherein
R' is a secondary alkyl of 3 to 5 carbon atoms,

R and R⁰ are independently hydrogen, fluoro, chloro, straight chain alkyl of 1 to 4 carbon atoms, straight chain alkoxy of 1 to 4 carbon atoms or trifluoromethyl, with the provisos that R is in the 5- or 6-position, and no more than one of R and R⁰ is trifluoromethyl, or R⁰ and R together form 4,5-alkylenedioxy of 1 to 2 carbon atoms, and Y and Y' are independently hydrogen, fluoro, chloro, straight chain alkyl of 1 to 4 carbon atoms, straight chain alkoxy of 1 to 4 carbon atoms or trifluoromethyl, with the proviso that no more than one of Y and Y' is trifluoromethyl, from a corresponding 2-aminobenzophenone of the formula:

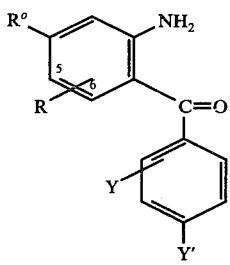

wherein R⁰, R, Y and Y' are as above defined, a borohydride, carboxylic acid and a ketone of the formula:

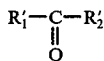

wherein $R_1'$ and $R_2'$ are each alkyl of 1 to 3 carbon atoms with the proviso that $R_1'$ and $R_2'$ do not exceed 4 carbon atoms, comprising forming a solution comprising said 2-aminobenzophenone, said ketone and a saturated carboxylic acid of 2 to 4 carbon atoms having a strength of from pH 3 to 5 as determined in a 98% by weight aqueous solution, adding to said solution at a temperature of at least 10° C. a borohydride at a rate controlled such that the resulting reaction solution does not exceed a temperature of 35° C., and maintaining a reaction temperature in the range of from 10° C. to 35° C. throughout the reaction, the mol ratio of borohydride to said 2-aminobenzophenone being in the range of from 1.7:1 to 4:1, the mol ratio of carboxylic acid to said 2-aminobenzophenone being at least 6:1 and the mol ratio of said ketone to 2-aminobenzophenone being at least 3:1, the actual amounts of said carboxylic acid, ketone and any other liquid present being such and proportioned to each other and to the 2-aminobenzophenone so that the reaction is carried out in a substantially homogeneous solution within said temperature range.

2. The process of claim 1 in which the borohydride is added at a temperature of at least 15° C. at a rate controlled such that the resulting reaction solution is maintained at a temperature not in excess of 30° C. and such that the temperature increase by reason of such addition does not exceed 5° C. in which the temperature is maintained in the range of from 15° C. to 30° C. throughout the reaction and in which the borohydride is added in finely divided form having a particle size which passes a No. 20 Tyler Standard Screen.

3. The process of claim 2 in which the borohydride is added at a temperature of at least 15° C. at a rate controlled such that the resulting reaction solution is maintained at a temperature not in excess of 28° C. and such that the temperature increase by reason of such addition does not exceed 2° C. and in which the temperature is maintained in the range of from 15° C. to 28° C. throughout the reaction.

4. The process of claim 1 in which the mol ratio of borohydride to 2-aminobenzophenone is from 2:1 to 3.2:1, the mol ratio of carboxylic acid to 2-aminobenzophenone is from 8:1 to 30:1 and the mol ratio of ketone to 2-aminobenzophenone is 8:1 to 30:1.

5. The process of claim 3 in which the mol ratio of borohydride to 2-aminobenzophenone is from 2:1 to 2.8:1, the mol ratio of carboxylic acid to 2-aminobenzophenone is from 10:1 to 20:1 and the mol ratio of ketone to 2-aminobenzophenone is from 10:1 to 20:1.

6. The process of claim 1 in which the carboxylic acid is acetic acid.

7. The process of claim 5 in which the carboxylic acid is acetic acid.

8. The process of claim 1 in which the solution contains no more than 8 percent water based on the weight of the carboxylic acid.

9. The process of claim 7 in which the solution contains no more than 5 percent water based on the weight of the acetic acid.

10. The process of claim 1 in which the borohydride is an alkali metal borohydride in which the alkali metal is the only metal.

11. The process of claim 9 in which the borohydride is an alkali metal borotetrahydride.

12. The process of claim 11 in which the borohydride is sodium borohydride or potassium borohydride.

13. The process of claim 1 in which the total reaction time does not exceed 10 hours.

14. The process of claim 12 in which the total reaction time is in the range of 1 to 4 hours.

15. The process of claim 14 in which the reaction solution contains between 0.1 and 2.5 percent water based on the weight of the carboxylic acid.

16. The process for preparing in at least 75% yield a 2-sec.-alkylaminobenzophenone of the formula:

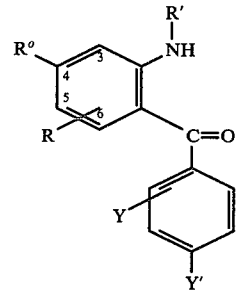

wherein

R' is a secondary alkyl of 3 to 5 carbon atoms,

R and R⁰ are independently hydrogen, fluoro, chloro, straight chain alkyl of 1 to 4 carbon atoms, straight chain alkoxy of 1 to 4 carbon atoms or trifluoromethyl, with the provisos that R is in the 5- or 6-position, and no more than one of R and R⁰ is trifluoromethyl, or R⁰ and R together form 4,5-alkylenedioxy of 1 or 2 carbon atoms, and Y and Y' are independently hydrogen, fluoro, chloro, are independently hydrogen, fluoro, chloro, straight chain alkyl of 1 to 4 carbon atoms, straight chain alkoxy of 1 to 4 carbon atoms or trifluoromethyl, with the proviso that no more than one of Y and Y' is trifluoromethyl,
comprising adding a borohydride to a homogeneous solution of an iminium derivative of the formula:

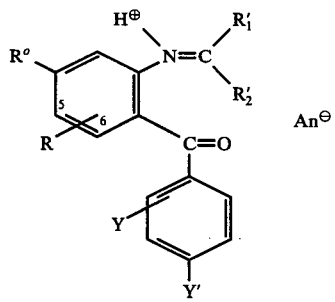

wherein $R^0$, R, Y and Y' are as above defined, wherein $R_1'$ and $R_2'$ are each alkyl of 1 to 3 carbon atoms with the proviso that $R_1'$ and $R_2'$ do not exceed 4 carbon atoms, and wherein An is the anionic form of a saturated carboxylic acid of 2 to 4 carbon atoms having a strength of from pH 3 to 5 as determined in a 98% by weight aqueous solution, at a temperature of at least 10° C. and at a rate controlled such that the resulting reaction solution does not exceed a temperature in the range of from 10° C. to 35° C. throughout the reaction, the mol ratio of borohydride is said iminium derivative being in the range of from 1.7:1 to 4:1, and said solution containing a saturated carboxylic acid as above defined in an amount such that the mol ratio of total carboxylic acid to said iminium derivative is at least 6:1, the total carboxylic acid presence being determined by the number of mols of carboxylic acid anions present in said solution.

17. The process of claim 16 in which the borohydride is added at a temperature of at least 15° C. at a rate controlled such that the resulting reaction solution is maintained at a temperature not in excess of 30° C. and such that the temperature increase by reason of such addition does not exceed 5° C., in which the temperature is maintained in the range of from 15° C. to 30° C. throughout the reaction and in which the borohydride is added in finely divided form having a particle size which passes a No. 20 Tyler Standard Screen.

18. The process of claim 17 in which the borohydride is added at a temperature of at least 15° C. at a rate controlled such that the resulting reaction solution is maintained at a temperature not in excess of 28° C. and such that the temperature increase by reason of such addition does not exceed 2° C. and in which the temperature is maintained in the range of from 15° C. to 28° C. throughout the reaction.

19. The process of claim 16 in which the mol ratio of borohydride to iminium derivative is from 2:1 to 3.2:1, the mol ratio of carboxylic acid to said iminium derivative is from 8:1 to 30:1 and in which said solution contains a ketone of the formula $R_1'COR_2'$, wherein $R_1'$ and $R_2'$ is as defined in claim 16 in a mol ratio to said iminium derivative of from 7:1 to 29:1.

20. The process of claim 19 in which the mol ratio of borohydride to said iminium derivative is from 2:1 to 2.8:1, the mol ratio of carboxylic acid is from 10:1 to 20:1 and the mol ratio of said ketone to said iminium derivative is from 9:1 to 19:1.

21. The process of claim 16 in which the carboxylic acid is acetic acid.

22. The process of claim 19 in which the carboxylic acid is acetic acid.

23. The process of claim 16 in which the solution contains no more than 8 percent water based on the weight of the carboxylic acid.

24. The process of claim 22 in which the solution contains no more than 5 percent water based on the weight of the acetic acid.

25. The process of claim 16 in which the borohydride is an alkali metal borohydride in which the alkali metal is the only metal.

26. The process of claim 24 in which the borohydride is added at a temperature of at least 15° C. at a rate controlled such that the resulting reaction solution is maintained at a temperature not in excess of 28° C. and such that the temperature increase by reason of such addition does not exceed 2° C. and in which the temperature is maintained in the range of from 15° C. to 28° C. through the reaction.

* * * * *